(12) United States Patent
Sachdeva et al.

(10) Patent No.: US 8,715,736 B2
(45) Date of Patent: May 6, 2014

(54) NANOPARTICLE FORMULATIONS FOR SKIN DELIVERY

(75) Inventors: Mandip Singh Sachdeva, Tallahassee, FL (US); Ram Patlolla, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 0 days.

(21) Appl. No.: 12/433,344

(22) Filed: Apr. 30, 2009

(65) Prior Publication Data

US 2012/0195957 A1    Aug. 2, 2012

(51) Int. Cl.
*A61K 9/14* (2006.01)
*A61K 9/51* (2006.01)

(52) U.S. Cl.
USPC ........... 424/489; 424/400; 514/946; 514/947; 977/773; 977/797; 977/801; 977/904; 977/906; 977/926

(58) Field of Classification Search
None
See application file for complete search history.

(56) References Cited

U.S. PATENT DOCUMENTS

| | | | |
|---|---|---|---|
| 2004/0063718 A1* | 4/2004 | Michaelis et al. | 514/252.13 |
| 2005/0058697 A1* | 3/2005 | Bally et al. | 424/450 |
| 2006/0014712 A1* | 1/2006 | Neuman | 514/44 |
| 2006/0083781 A1* | 4/2006 | Shastri et al. | 424/450 |

OTHER PUBLICATIONS

VP Torchilin, R Rammohan, V Weissig, TS Levechenko. "TAT peptide on the surface of liposomes affords their efficient intracellular delivery even at low temperature and in the presence of metabolic inhibitors" Proceedings of the National Academy of Sciences, vol. 98 No. 15, Jul. 17, 2001, pp. 8786-8791.*

SR Yang, SB Kim, CO Joe, JD Kim. "Intracellular delivery enhancement of poly(amino acid) drug carriers by oligoarginine conjugation." Journal of Biomedical Materials Research Part A, vol. 86(1), 2008, pp. 137-148, available online Oct. 23, 2007.*

V Jenning, AF Thunemann, SH Gohla. "Characterisation of a novel solid lipid nanoparticle carrier system based on binary mixtures of liquid and solid lipids." International Journal of Pharmaceutics, vol. 199, 2000, pp. 167-177.*

SW Jones, R Christison, K Bundell, CJ Voyce, SMV Brockbank, P Newham, MA Lindsay. "Characterisation of cell-penetrating peptide-mediated peptide delivery." British Journal of Pharmacology, vol. 145, 2005, pp. 1093-1102.*

* cited by examiner

*Primary Examiner* — Frederick Krass
*Assistant Examiner* — Isaac Shomer
(74) *Attorney, Agent, or Firm* — Parks IP Law LLC; Collen A. Beard, Esq.

(57) ABSTRACT

Methods and formulations for treating a condition of the skin by delivering therapeutic formulations to the skin that translocates active substances across the stratum corneum barrier to a targeted skin tissue. The methods and formulations comprise active substances encapsulated within surface modified nanostructured lipid carrier nanoparticles.

10 Claims, 5 Drawing Sheets

NANOPARTICLE FORMULATIONS FOR SKIN DELIVERY

STATEMENT REGARDING FEDERALLY SPONSORED RESEARCH OR DEVELOPMENT

This research was supported by the National Institutes of Health/NIAMS grant number 36458.

FIELD OF THE INVENTION

The invention relates to topical or transdermal delivery of an active substance or drug across the stratum corneum barrier to a targeted skin tissue and formulations thereof.

BACKGROUND OF THE INVENTION

Topical or transdermal drug delivery has several advantages over the conventional oral and intravenous dosage forms. Some advantages of topical or transdermal drug delivery are the prevention of first pass metabolism, minimization of pain, and possible controlled release of drugs. There is a growing interest in the optimization of drug delivery targeted to a physiological site in the skin. Barry, B. W., *Novel Mechanisms and Devices to Enable Successful Transdermal Drug Delivery*, Eur. J. Pharm. Sci. 2001, 14, 101-114. Several attempts have been made and are still under investigation to develop a topical formulation for micro and macromolecules for the treatment of skin diseases. However, the success in developing a topical delivery formulation will depend on the ability of a drug to permeate the skin in sufficient quantity to achieve its desired therapeutic effects. Most drug candidates alone are not capable of achieving the desired therapeutic effects because they are unable to cross the stratum corneum, and therefore require physical enhancers or special transporters to enter into the skin. Trommer, H. et al., *Overcoming the Stratum Corneum: The Modulation of Skin Penetration*, Skin Pharmacol. Physiol. 2006, 19, 106-121.

Chemical enhancers are widely used for the topical delivery of active agents because they modulate the penetration of macromolecules across the skin, but most of them have limited success. Barry, B., *Breaching the Skin's Barrier to Drugs*, Nat. Biotechnol. 2004, 22, 165-167, and Prausnitz, M. R., et al., *Transdermal Drug Delivery*, Nat. Biotechnol. 2008, 26, 1261-1268. It has been shown that the permeation of melatonin across the skin can be increased significantly using chemical penetration enhancers in solution formulations. Rachakonda V K, et al., *Screening of Chemical Penetration Enhancers for Transdermal Drug Delivery Using Electrical Resistance of Skin*, Pharm Res. 2008, 25(11), 2697-704, and Sapra B, et al., *Percutaneous Permeation Enhancement by Terpenes: Mechanistic View*, AAPS J. 2008, 10(1), 120-32. The use of chemical penetration enhancers, such as fatty alcohols and fatty acids, increased the permeation of melatonin across the skin; however, the enhancement of permeation was dependent on the chemical structure of the enhancers.

Techniques such as electroporation, iontophoresis and microneedles have also been used to enhance the skin permeation of active ingredients. Prausnitz, M. R., et al., *Transdermal Drug Delivery*, Nat. Biotechnol. 2008, 26, 1261-1268, and Kolli, C. S., et al., *Characterization of Solid Maltose Microneedles and Their use for Transdermal Delivery*, Pharm. Res. 2008, 25(1), 104-13. However, each of these techniques has its respective problems in terms of toxicity and therapeutic feasibility.

Other delivery techniques include the use of nanoparticle delivery systems, which are known to be biocompatible and protect the active ingredient from degradation. Among the various nanoparticle systems, lipid nanoparticles are thought to be promising as drug carrier systems for skin application. Melt-emulsified nanoparticles based on lipids which are solid at room temperature have several advantages over nanoemulsions, nanosuspensions, mixed micelles, polymeric nanoparticles and liposomes. The advantages of these solid lipid nanoparticles (SLN) are that they protect the active ingredients from enzymatic degradation, prevent transepidermal water loss and release the drugs in a controlled manner for prolonged periods and thereby enhance the therapeutic effect. Jenning, V., et al., *Vitamin A-Loaded Solid Lipid Nanoparticles for Topical use: Drug Release Properties*, J. Control. Release. 2000, 66, 115-126. The stabilization of chemically unstable drugs by incorporation into a lipid matrix and also sustained release is possible due to the solid matrix properties of solid lipid nanoparticles (SLN). Souto, E. B., et al., *Development of a Controlled Release Formulation Based on SLN and NLC for Topical Clotrimazole Delivery*, Int. J. Pharm. 2004, 278, 71-77, Muller, R. H., et al., *Cytotoxicity of Solid Lipid Nanoparticles as a Function of the Lipid Matrix and the Surfactant*, Pharm. Res. 1997, 14, 458-462, and Wissing, S. A., et al., *Investigations on the Occlusive Properties of Solid Lipid Nanoparticles (SLN)*, J. Comet. Sci. 2001, 52, 313-323.

SLNs are composed of physiological lipids with low toxicity profile and may potentially find application not only in cosmetic and dermatological preparations but even in parenteral and oral drug formulations. Almeida, A. J., et al., *Solid Lipid Nanoparticles as a Drug Delivery System for Peptides and Proteins*, Adv. Drug Deliv. Rev. 2007, 59, 478-490 and Muller, R. H., et al., *Solid Lipid Nanoparticles (SLN) and Nanostructured Lipid Carriers (NLC) in Cosmetic and Dermatological Preparations*. Adv. Drug Deliv. Rev. 2002, 54, 131-155. Many drugs have been successfully incorporated into SLNs, but their use is restricted due to low drug loading, and drug expulsion from the carrier which leads to a decrease in the chemical stability of the drug molecule during storage.

In order to decrease the degree of organization of the lipid matrix in SLN, and the drug loading, carrier nano lipid crystal nanoparticles (NLCN) were developed and are known as the second generation of lipid nanoparticles. Pardeike, J., et al., *Lipid Nanoparticles (SLN, NLC) in Cosmetic and Pharmaceutical Dermal Products*, Int. J. Pharm. 366 (1-2) (2009) 170-184. Based on the chemical nature of the lipid molecules, the inner structure of NLCNs differs from that of SLNs, in that NLCNs are composed of mixtures of solid and liquid lipids (oils), whereas SLNs are composed only of solid lipids. Because the solubility of active ingredients in oils is generally much higher than in solid lipids, higher drug loading capacity and minimal expulsion during storage is achieved by NLCNs. Lopes, L. B., et al., *Comparative Study of the Skin Penetration of Protein Transduction Domains and a Conjugated Peptide*. Pharm. Res. 2005, 22(5), 750-757. While this new generation of NLCNs is believed to enhance delivery, it has been shown that these particles do not cross the stratum corneum barrier. As a result of the occlusive property of the particles, the particles reside in the stratum corneum and release the drug into the epidermis. Wang, J. J., et al., *Skin Permeation of Buprenorphine and its Ester Prodrugs from Lipid Nanoparticles: Lipid Emulsion, Nanostructure Lipid Carriers and Solid Lipid Nanoparticles*. J. Microencapsul. 2009, 12, 1-14, Fang, J. Y., et al., *Lipid Nanoparticles as Vehicles for Topical Psoralen Delivery: Solid Lipid Nanoparticles (SLN) Versus Nanostructured Lipid Carriers (NLC)*. Eur. J. Pharm. Pharm. Biopharm. 2008, 70 (2), 633-640, and Joshi, M., et al., *Nanostructured Lipid Carrier (NLC) Based Gel of Celecoxib*. Int.

J. Pharm. 2008, 346 (1-2), 124-132. Thus, there is a dire need to develop useful NLCNs to treat skin disorders by permeating the skin and delivering the active substance to a target site that lies in the deep epidermis.

It is well known that it is a difficult task to deliver active substances across the skin due to the barrier function of the skin provided by the highly organized structure of the stratum corneum (SC). The use of several techniques, including cell penetrating peptides (CPP) or cell transduction domains or membrane transduction peptides are emerging as attractive drug delivery tools because of their ability to translocate micro and macromolecules across the cell membrane. Patel, L. N., et al., *Cell Penetrating Peptides: Intracellular Pathways and Pharmaceutical Perspectives*. Pharm. Res. 2007, 24(11), 1977-92. CPPs have been used to deliver proteins, oligonucleotides, solid lipid nanoparticles, and liposomes into tumor cells. Masterobattista, E., et al., Functional *Characterization of an Endosome Disruptive Peptide and its Application in Cystolic Delivery of Immoliposome-Entrapped Proteins*. J. Biol. Chem. 2002, 277, 27135-27143, Astriab-Fisher, A., et al., *Conjugates of Antisense Oligonucleotides With the Tat and Antenapedia Cell-Penetrating Peptides: Effects on Cellular Uptake, Binding to Target Sequences, and Biologic Actions*. Pharm. Res. 2002, 19, 744-754, Rudolph, C., et al., *Application of Novel Solid Lipid Nanoparticle (SLN)-Gene Vector Formulations Based on a Dimeric HIV-1-TAT-Peptide In Vitro and In Vivo*. Pharm. Res. 2004, 21(9), 1662-1669, and Fretz, M. M. et al., *OVCAR-3 Cells Internalize TAT-Peptide Modified Liposomes by Endocytosis*. Biochim. Biophys. Acta. 2004, 1665, 48-56. Despite progress in the field, topical and transdermal delivery of peptides and proteins in therapeutics remains difficult.

It has been shown (Lopes, L. B. at 750-757) that CPPs can enhance the skin permeation of cyclosporine and P20 peptides when they are conjugated to the CPP; however, these CPPs are primarily composed of arginine and lysine residues, which confer a positive charge to the CPP. Furthermore, there are several available CPPs that have membrane translocating capability based on their arginine content. Among the cell-penetrating peptides, TAT peptide is known and extensively used for drug delivery. It has been shown that TAT or YARA cell penetrating peptide mediated translocation of P20 peptide across the human skin is very small. Lopes, B. L., at al., *Comparative Study of the Skin Penetration Transduction Domains and a Conjugated Peptide*, Pharm. Res. 2005, 22, 750-757. However, there is still debate as to whether cell penetrating peptides are capable of translocating the lipid pay load across the skin layers, when the molecule is not conjugated.

None of above discussed references has focused on the delivery of non-conjugated molecules or active substances, or the permeation of CPP surface coated NLCNs into the skin. We have discovered that coating of nanoparticles with CPP enhances the permeation of drug several fold into stratum corneum and epidermis. More particularly, our results show that coating of NLCs with CPP enhances skin permeation of celecoxib by 3-4 fold when compared to non-coated and non-specific CPP coated nanoparticles. Furthermore, we show that the co-localization of FITC labeled CPP and DID encapsulated NLC in the epidermal layers indicates that surface modification of nanoparticles with CPP is an added advantage in delivering a greater amount of nanoparticles or drug into the skin.

SUMMARY OF THE INVENTION

In accordance with the purpose(s) of this invention as embodied and broadly described herein, this invention relates to methods of topical or transdermal delivery of surface modified nanostructured lipid carrier nanoparticles, encapsulating an active substance, targeted to the skin tissue of a subject and formulations thereof.

In one aspect, this invention relates to method of delivering an active substance to a subject, said method comprising:
selecting a target skin tissue in the skin of the subject;
providing a plurality of nanostructured lipid carrier nanoparticles, comprising an active substance encapsulated within the nanoparticles,
modifying a surface of the nanostructured lipid carrier nanoparticles with a drug delivery enhancer; and
topically administering surface modified nanostructured lipid carrier nanoparticles comprising the encapsulated active substance to the skin of the subject so that the nanostructured lipid carrier nanoparticles penetrate the skin and are delivered to said selected target skin tissue.

In another aspect, this invention relates to a formulation for topical application to a selected target skin tissue in the skin of the subject, wherein said formulation comprises nanostructured lipid carrier nanoparticles encapsulating an active substance, wherein a surface of the nanoparticles is modified with a drug delivery enhancer.

In yet another aspect, the invention relates to a method of delivering an active substance to a subject, said method comprising:
selecting a target skin tissue in the skin of the subject;
providing a lipid based particulate carrier system, comprising an active substance encapsulated within the lipid based particulate carrier system,
modifying a surface of the lipid based particulate carrier system with a drug delivery enhancer; and
topically administering the surface modified lipid-based particulate carrier system comprising the encapsulated active substance to the skin of the subject so that the lipid based particulate carrier system penetrates the skin and is delivered to said selected target skin tissue.

DETAILED DESCRIPTION OF THE INVENTION

The invention is described herein in detail using the terms defined below unless otherwise specified.

It must be noted that as used in the specification and the appended claims, the singular forms "a" "an" and "the" include plural referents unless the context clearly dictates otherwise.

Ranges are often expressed herein as from "about" one particular value, and/or to "about" another particular value. When such a range is expressed, another embodiment includes from the one particular value and/or to the other particular value. Similarly, when values are expressed as approximation, by use of the antecedent "about," it will be understood that the particular value forms another embodiment.

The structure of skin is such that it naturally protects the body from the entry of foreign material such as microorganisms and chemicals, and from the loss of endogenous material such as water, Skin has a multi-layered structure, with each layer of skin representing different levels of cellular or epidermal differentiation.

The term "stratum corneum" ("hereinafter SC") refers to the external layer of the epidermis. The epidermis is the outermost layer, which consist primarily of layers of keratinized epithelium, under which lies the dermis, a layer of connective tissue which contains a rich network of the blood and lymph vessels, hair follicles and sweat and sebaceous glands.

Dermal delivery is the delivery of an agent (e.g., an active substance) to the skin (epidermis, including stratum corneum and dermis) via topical application to the skin surface. In contrast, transdermal delivery is the delivery of an agent (e.g., an active substance), again via topical application to the skin surface, but in this case through the various layers of the dermis and into the systemic circulation. Dermal delivery provides an advantage over several other delivery techniques in that it allows for the direct administration of the active substance to a selected target skin tissue in a subject.

The terms "nanostructured lipid carrier nanoparticles" (NLCN or NLCNs) or "nanostructured lipid carrier" (NLC) are used interchangeably and are meant to describe the plurality of lipid carrier nanoparticles forming the nanostructure. The lipid carrier nanoparticles in the nanostructure are produced using blends of solid lipids and liquid lipids (oils). To obtain blends for the particles in the nanostructure, solid lipids are mixed with liquid lipids in a desired ratio. The blends obtained are solid at body temperature. These NLCNs can encapsulate active substances. NLCNs can be produced by known hot or cold high pressure homogenization techniques.

Exemplary oil-based or lipidic medium carriers for the NLCN are mono-, di- and triglycerides or mixtures thereof, and nickel chelating compounds. In a preferred embodiment, the oil-based or lipidic medium carrier may be COMPRITOL 888 ATO brand, MIGLYOL 812 brand, and DOGS-NTA-Ni chelating lipid and the like.

Exemplary liquid lipids for the NLCN are surfactants such as TWEEN 80 and the like.

As used herein, the term "nanoparticle" refers to particles composed having a matrix-type structure with a size of less than about 200 nanometers, preferably from about 160 nanometers to about less than 200 nanometers. When the nanoparticles include an active substance, the active substance is embedded or encapsulated in the matrix-type structure of the nanoparticles. Nanoparticles of the present invention can be irregular, oblong, spindle, rod, cylindrical, pancake, dicoid. spherical, bioconcave or red blood cell-shaped.

A nanoparticle or particulate of this invention has an active substance encapsulated within the nanoparticles forming the nanostructure or carrier system. Methods of preparing nanoparticles that include an active substance encapsulated within are known to those skilled in the art.

As used herein, "encapsulated within" means the active substance is contained substantially inside the nanoparticle.

Modifying a surface of the nanostructured lipid carrier nanoparticles refers to the method of coating the outside of the surface of the nanoparticles with a drug delivery enhancer. More specifically, the surface is modified by engraftment intern coating of the drug delivery enhancer onto the nanoparticle, i.e., coating a TAT cell penetrating peptide onto the nanoparticle surface. The engraftment can be accomplished by using, for example, DOGS-NTA-Ni chelating/spacer lipid, wherein the DOGS (lipid portion of the spacer) is embedded in the preformed nanoparticle, and the NTA-Ni portion/tail of the spacer is projected outside of the nanoparticle surface such that the 6 histidine section on the TAT cell penetrating peptide bonds strongly to the NTA-Ni portion/tail to form a nanoparticle with a NTA-Ni-6Histidine-CPP surface. It is well known in the field that the histidine tag binds to NTA-Ni. The surface modification of the inventive nanoparticles can also be accomplished by utilizing methods such as maleimide chemical conjugation and chemical conjugation of CPP to the nanoparticle surface using PEG spacers, or other suitable methods. The preformed nanoparticles are coated as described and incubated for a period of time such that a bond is formed between the 6 histidine tag and NTA-Ni.

The term "drug delivery enhancer" is used to describe a drug delivery agent that is used to translocate micro and macromolecules across cell membranes. Exemplary drug delivery agents are cell penetrating peptides, also known as cell transduction domains, such as transactivating transcriptional activating protein (TAT) and YARA (YARAAAR-QARA) (SEQ ID NO 2), polyarginines (Rn), wherein Rn is $Arg_8$ (SEQ ID NO 3), $Arg_{11}$ (SEQ ID NO 4), or $Arg_{15}$ (SEQ ID NO 5), and penetratin. In a preferred embodiment, the TAT is 6His TAT peptide (Tyr-Gly-Arg-Lys-Lys-Arg-Arg-Gln-Arg-Arg-Arg-His-His-His-His-His-His) (SEQ ID No 1).

The term "lipid-based particulate" refers to microscopic particles whose size is less than about 200 nanometers, preferably from about 160 nanometers to about less than about 200 nanometers. The particulate of the invention can be irregular, oblong, spindle, rod, cylindrical, pancake, dicoid, spherical or red blood cell-shaped.

The term "liposome" is a type of lipid-based particulate and refers to a compartment that is completely enclosed by a lipid bilayer typically composed of phospholipids. Liposomes are prepared according to standard techniques known to those skilled in the art.

Emulsions, polymeric, silica, or gold nanoparticles carrier systems may also be encapsulated with an active agent and modified on the surface with a drug delivery enhancer for topical applications.

Examples of suitable polymeric nanoparticles are PLGA, poly(D,L-lactide-co-glycolide), poly(D,L-lactide), poly(D, L-lactide-co-lactide), poly(L-lactide), poly(glycolide), poly (L-lactide-co-glycolide), poly(caprolactone), poly(glycolide-co-trimethylene carbonate), poly(3-hydroxybutyrate), poly(3-hydroxybutyrate-co-3-hydroxyvalerate), poly(4-hydroxybutyrate), poly(ester amide), poly(ester-sulfoester amide), poly(orthoester), poly(anhydride), and polysaccharides such as alginate and chitosan.

The term "delivery" means the introduction of a foreign agent, i.e., the active substance into a cell. In a preferred embodiment, the surface modified nanostructured lipid carrier nanoparticles may be used to topically (e.g., penetrate in the skin) or transdermally (e.g., permeate across the stratum corneum barrier into the epidermis) deliver the active substance.

The term "administration" means the introduction of a foreign agent, i.e., the active substance into the skin. The term is intended to be synonymous with the term "delivery." Administration also refers to the methods of delivery of NLCN or particulate carriers of the invention (e.g., routes of administration such as, without limitation, topical, transdermal or dermal). The preferred method of delivery is transdermal or topical.

The term "treating" means the prevention, reduction, or partial or complete alleviation or cure of a disease or condition. In a preferred embodiment, the disease or condition treated is psoriasis, irritant contact dermatitis, atopic dermatitis, contact dermatitis, inflammation, eczema, infections including bacterial and fungal infections, acne, rheumatoid arthritis, skin cancer, statis dermatitis, seborrheic dermatitis, wound healing, and autoimmune disorders, such as bullous pemphigoid, pemphigus, rheumatoid arthritis and systemic lupus.

The term "subject" as used herein refers to any vertebrate animal, preferably a mammal, and more preferably a human.

The terms "active substance", "bioactive agent" and "drug" are used interchangeably, and refer to a wide array of different substances useful in the therapeutic, prophylactic or diagnostic treatment of humans or animals. Representative examples of active substance are anti-inflammatory drugs, anti-cancer agents, anti-psoriatic agents, analgesic agents, antibacterial agents, antibiotics, antiparasitic agents, antiviral agents, proteins, peptides, nucleosides, nucleotides, enzymes, hormones, neurotransmitters, glycoproteins, immunoglobins, local anesthetics, as well as other micro and macromolecules, and combinations thereof. In a preferred embodiment, the active substance may be selected from non-steroidal anti-inflammatory drugs (e.g., celecoxib, ibuprofen, diclofenac, indomethacin, peroxicam, ketoprofen, and naproxen) and steroidal anti-inflammatory drugs (e.g., prednisone, prednisolon, and hydrocortisone) in a pharmaceutically effective amount. Exemplary proteins for this invention are DNA, SiRNA or oligonucleotides. The active substance may be delivered to the skin, including the stratum corneum, the other layers of the epidermis and the dermis. In a preferred embodiment, the active substance is delivered primarily to the epidermis to a depth of about 80 to about 120 microns.

As used herein, the term "effective amount" refers to an amount of active substance sufficient to bring about the treatment for which said substance is administered.

As used herein the terms "peptide", "protein" and "polypeptide" are used interchangeably and refer to a compound made up of a chain of amino acid residues linked by peptide bonds. The sequence for peptides is given in the order from the amino terminus to the carboxyl terminus.

The term "localized to the skin" means restricted to a specific body part or region of the body.

The term "partially localized to the skin" means partially restricted to a specific body part or region of the body.

In one embodiment, the topically administered surface modified nanostructured lipid carrier nanoparticles formulations may release the active substance in a sustained or controlled manner upon application to the skin.

In general, the formulation is prepared by uniformly and intimately bringing into association the active substance with the nanostructured lipid carrier nanoparticles (e.g., oil-based or lipidic medium carrier) and organic phase, and subjecting the oil-in-water dispersion to high pressure homogenization at a desired temperature for a period of time forming the associated mixture into nanoparticles. The surface of the pre-formed nanoparticle is then coated with the CPP by incubating with the desired amount of CPP for about 30 minutes at room temperature to form the desired active substance-NLCNs.

The examples below serve to further illustrate the invention, to provide those of ordinary skill in the art with a complete disclosure and description of how the formulations or methods herein are made and evaluated, and are not intended to limit the scope of the invention. In the examples, unless expressly stated otherwise, amounts and percentages are by weight, temperature is in degree Celsius or is at ambient temperature, and pressure is at or near atmospheric.

EXAMPLES

Materials

Celecoxib (CXB) was provided by Pfizer (Skokie, Ill.). The triglyceride Miglyol 812 was obtained from Sasol Germany GmbH (Witten, Germany) and Compritol 888 ATO was provided by Gattefosse (Saint Priest, France). The phospholipids 1-palmitoyl-2-oleoyl-phosphatidylcholine (POPC), 1,2-dioleoyl-sn-glycero-3-phosphoethanolamine (DOPE) and 1,2-di-(9Z-octadecenoyl)-sn-glycero-3-[(N-(5-amino-1-carboxypentyl)iminodiacetic acid)succinyl] (nickel salt) (DOGS-NTA-Ni) were purchased from Avanti Polar Lipids (USA). Cholesterol, Tween 80, pH 7.4 phosphate buffer saline (PBS), paraformaldehyde, tetrahydrofuran (THF), trifluoro acetic acid (TFA), and dialysis membranes (molecular weight cut off 12,400 daltons and flat width of 23 mm) were procured from Sigma-Aldrich Chemicals (St. Louis, USA). Polyoxyethylene-20 oleyl ether or Volpo-20 (Oleth-20) was a kind gift from Croda Inc (New Jersey, USA). Vivaspin centrifuge filters (molecular weight cut off 10,000 Daltons) was procured from Sartorius Ltd, (Stonehouse, UK). All other chemicals used herein were of analytical grade. All of the CPP peptides were synthesized by GenScript Corporation (NJ, USA). See Table 1 below for details of the composition, molecular weight and iso-electric points of the CPPs. Fluorescent Isothiocyanate (FITC), DID-oil and DIO fluorescent dyes were procured from Invitrogen (USA).

TABLE 1

CPP Peptide Sequence

| Sequence | Molecular weight | Short form | Iso-electric point |
|---|---|---|---|
| TAT peptide:<br>Tyr-Gly-Arg-Lys-Lys-Arg-Arg-Gln-Arg-Arg-<br>Arg-His-His-His-His-His-His or<br>(YGRKKRRQRRRHHHHHH)<br>(SEQ ID NO 1) | 2382.71 | TAT | 12.7 |
| Control peptide (YKA)<br>YKALRISRKLAKHHHHHH<br>(SEQ ID NO 6) | 2269.7 | YKA | 11.6 |
| Poly Arginine (R)<br>RRRRRRRRHHHHHH<br>(SEQ ID NO 3) | 2090.4 | R8 | 13.2 |
| Poly Arginine (R)<br>RRRRRRRRRRRHHHHHH<br>(SEQ ID NO 4) | 2558.9 | R11 | 13.4 |
| Poly Arginine (R)<br>RRRRRRRRRRRRRRRHHHHHH<br>(SEQ ID NO 5) | 3183.7 | R15 | 13.5 |

Example 1

Preparation of Nanoparticles Encapsulating Fluorescent Dye

Step 1: General Method of Preparing Nanoparticles:

For tracking nanoparticles in the skin two types of fluorescent dyes were used, DID-oil (Excitation/Emission: 644-665 nm) or DIO dye (Excitation/Emission: 484-501 nm); both dyes are lipophilic. Fluorescent dye encapsulated formulations were prepared by hot melt homogenization technique as described in C. Puglia, et al., *Lipid Nanoparticles for Prolonged Topical Delivery An In-Vitro and In-Vivo Investigation*, Int. J. Pharma., 357 (2008) 295-304. In brief, fluorescent dye was dissolved in dichloromethane (0.5 ml) and mixed with the lipid phase comprised of Compritol 888 ATO, DOGS-NTA-Ni and Miglyol 812. The organic phase was removed on a rota evaporator for 2-3 hours at 80° C. To the heated lipid phase 20 ml of an aqueous solution containing Tween 80, a surfactant, was added at the same temperature under high speed mixing (20,000 rpm for 1 minute). The resultant oil-in-water dispersion was passed through an Emulsiflex-C5 (Avestin, Ottawa, Canada) high-pressure homogenizer at 5000 psi for 5-6 cycles, Throughout the process the temperature was maintained at 80° C. The composition of these NLCN systems is demonstrated in Table 2.

TABLE 2

Fluorescent dye Encapsulated NLC-NTA Formulation

| Ingredients | Quantity (milligrams) |
|---|---|
| DID-oil or DIO dye | 0.5 |
| Compritol 888 | 700 |
| Miglyol 812 | 300 |
| DOGS-NTA-Ni | 2 |
| Tween 80 | 480 |
| Distilled water up to | 25 ml |

Step 2: Coating the Surface of the Preformed Nanoparticles:

The surface of the above performed nanoparticles was coated with a cell penetrating peptide by incubating the above performed nanoparticles with a cell penetrating peptide for 30 minutes at room temperature.

Example 2

Visualization of Fluorescent Labeled Nanoparticles Skin Permeation Using Confocal Microscopy The fluorescent dye encapsulated, NLC-DID or NLC-DIO, nanoparticles were prepared according to Example 1 based on the formulation provided in Table 2. The particle size and zeta potential were measured with Brookhaven Instrument (USA). The particle size of the nanoparticles was found to be 173 nm and zeta potential was −11.7 mV; the addition of DID-oil and DIO dye did not change the zeta potential. The particle size range of the nanoparticle formulation in all batches was in the range of 160±20 mm In Vitro Skin Permeation and Distribution Analysis:

Hairless rats (CD® (SD) HrBi, Male) were sacrificed by an overdose of halothane anesthesia and the skin from the dorsal surface was excised and the adherent fat and subcutaneous tissue were removed. The full thickness skin was mounted between the donor and receptor compartments of the Franz diffusion cells (Permegear Inc., Riegelsville, Pa.) with the stratum corneum facing the donor compartment. Each cell had a diffusional surface area of 0.636 $cm^2$. For each type of fluorescent nanoparticles, 200 μl (75.69 μM DOGS-NTA-Ni) of formulation was incubated with 76 μM of cell penetrating peptide for 30 minutes at room temperature. The CPPs used were TAT, R8, and YKA (See Table 1). The formulation (200 μl) was applied onto the stratum corneum side in the donor compartment. The receptor compartment was filled with 5.2 ml of 10% ethanol in PBS (pH 7.4). The temperature of the receptor compartment was maintained at 37±0.1° C. with an external, constant temperature circulator water bath. After the incubation, the formulations were placed on the skin and at regular intervals (4 and 24 hours) the skin was blotted dry with Kimwipes. The skin (0.636 $cm^2$) was punched out with a biopsy punch. The skin tissue was frozen at −30° C. on a cryobar stage and sectioned with a Cryotome (Thermo-Shandon, 620 Electronic, (Waltham, Mass.) into 30 µm thick sections containing all three skin layers. The fluorescence associated with the skin was visualized using confocal microscope.

Results:

The permeation of fluorescent nanoparticles was tracked using confocal microscope (10× objectives) and the results are shown in FIGS. 1-7. The Figures provide images of rat skin permeation of DID-fluorescent dye encapsulated with and without FITC labeled CPP coated NLC-NTA nanoparticles. Skin sections of 30 microns were observed and all imaging conditions were similar.

Example 3

Celecoxib Encapsulated NLC Formulations and Surface Modification for Skin Permeation Celecoxib encapsulated nanoparticles (CXB-NLC) were prepared in accordance with Example 1, however the fluorescent dye was replaced with celecoxib (CXB). The composition of the formulation is provided in Table 3. For comparison, CXB solution formulation was prepared by dissolving 5 mg of CXB in 1 ml of ethanol and the volume was made to 10 ml with polyethylene glycol 400 (PEG400), because CXB is lipophilic and insoluble in water.

TABLE 3

CXB-NLC Formulation

| Ingredients | Quantity (milligrams) |
| --- | --- |
| Celecoxib | 20 |
| Compritol 888 | 700 |
| Miglyol 812 | 300 |
| DOGS-NTA-Ni | 2 |
| Tween 80 | 480 |
| Distilled water up to | 25 ml |

The encapsulated CXB-NLC nanoparticle formulation was modified with CPP as described in Example 1, and skin permeation studies were carried out for 24 hours by placing 200 µl of formulations (≈100 µg of CXB) on the donor compartment. The receptor fluid selected was 0.1% w/v Volpo 20 in pH 7.4 PBS, where the saturation solubility of CXB in 0.1% Volpo 20 was found to be 30 µg/ml. The Franz diffusion setup was similar as discussed above. The skin permeation studies were carried out on full thickness hairless rat and dermatomed human cadaver skin (obtained from HAM and Allsource, USA). The thickness of dermatomed human cadaver skin was 0.35 mm and rat skin was full thickness skin.

The skin tissue was frozen at −60° C. on a cryobar stage and sectioned with a Cryotome (Thermo-Shandon, 620 Electronic, (Waltham, Mass.) into SC, epidermis and dermis sections. Two sections of 10 µm thick were taken as SC, three sections of 45 µm thick were collected to represent the epidermis. Because the collection of the SC using the tape stripping method is difficult, both SC and epidermis will come together with this method. Celecoxib was extracted from stratum corneum, epidermis and dermis by adding 250 µl of 0.1 molar acetic acid and boiled for 15-20 minutes. After cooling to room temperature, 250 µl of acetonitrile was added and vortexed for 2 minutes, centrifuged at 13,200 rpm for 30 minutes. The supernatant was collected and the CXB content in the skin samples was analyzed with HPLC. The experiments were performed in triplicate.

Characterization of Nanoparticles

The particle size and zeta potential of CXB-NLC formulations were measured using Brookhaven Instrument (Holtsville, N.Y.) and the results are shown in Table 4.

TABLE 4

Particle size and zeta potential

| Formulation | Particle Size | Polydispersity Index | Zeta potential (mV) | Entrapment |
| --- | --- | --- | --- | --- |
| CXB-NLC | 167 nm | 0.207 | −25.01 | 98% |

To verify the total amount of drug present in the system, 0.1 ml of the CXB-NLC formulation was dissolved in 0.9 ml of tetrahydrofuran (THF) and subsequent dilutions were made with acetonitrile. Prior to the HPLC analysis for celecoxib content, the samples were centrifuged at 13,200 rpm for 15 minutes and 100 µl of supernatant was injected into the HPLC apparatus.

HPLC Analysis of Celecoxib:

The HPLC analysis was performed on a Waters system consisting of an autosampler (model 717 plus), binary pump (model 1525), and Waters UV photodiode array detector (model 996). A mobile phase consisting of acetonitrile/water (60:40) was pumped through the Symmetry C18 column (5 µm, 4.6×250 min) at a flow rate of 1.0 ml/min and the eluent was monitored at 254 nm. The entrapment efficiency was determined as described in R. R. Patlolla, et. al., *Pharmacokinetics and Tissue Distribution of Etoposide Delivered in Parenteral Emulsion*, J. Pharm. Sci., 94 (2005) 437-45.

The entrapment results (Table 4) and differential scanning calorimetry results indicate that most of the CXB was associated with the nanoparticles and about more than 90% of the drug was entrapped or associated with the nanoparticles.

Figure 1:
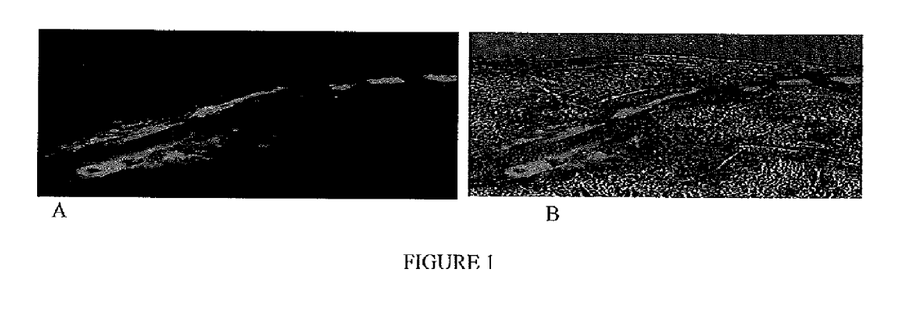
FIG. 1 illustrates rat skin permeation analysis of NLC (without NTA) microparticles encapsulating DIO dye over a 4 hour period. 1A illustrates the regular image and 1B illustrates the bright field image.
Figure 2:
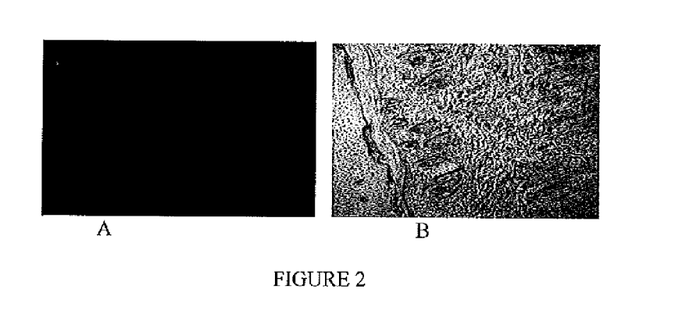
FIG. 2 illustrates rat skin permeation analysis of NLC-NTA microparticles encapsulating DID-oil dye over a 4 hour period. 2A illustrates the regular image and 2B illustrates the bright field image.
Figure 3:
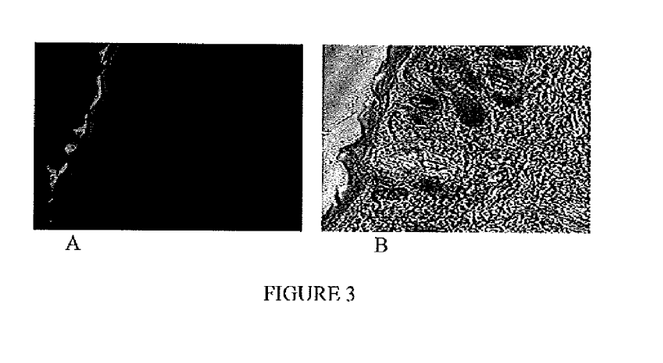
FIG. 3 illustrates rat skin permeation analysis of NLC-TAT microparticles encapsulating DID-oil dye over a 4 hour period. 3A illustrates the regular image and 3B illustrates the bright field image.
Figure 4:
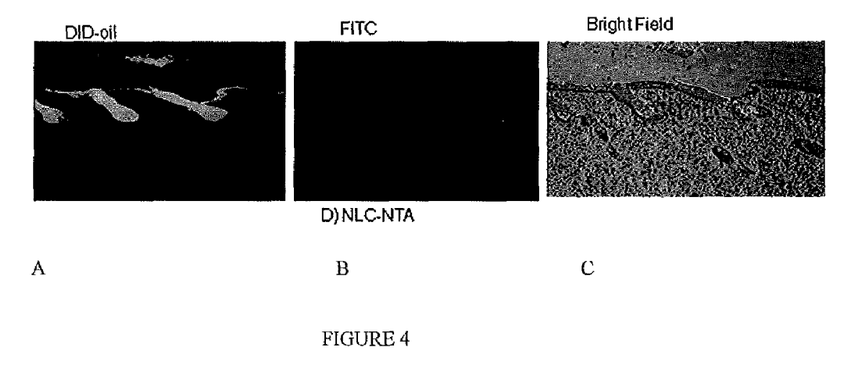
FIG. 4 illustrates rat skin permeation analysis of NLC-NTA microparticles encapsulating DID-oil dye over a 24 hour period. 4A illustrates the regular image, 4B illustrates the FITC labeled particles, and 4C illustrates the bright field image.
Figure 5:
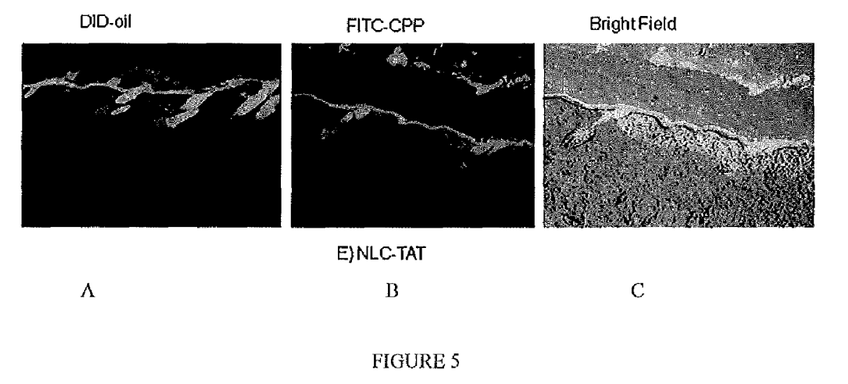
FIG. 5 illustrates rat skin permeation analysis of NLC-TAT microparticles encapsulating DID-oil dye over a 24 hour period. 5A illustrates the regular image, 5B illustrates the FITC labeled particles, and 5C illustrates the bright field image.
Figure 6:
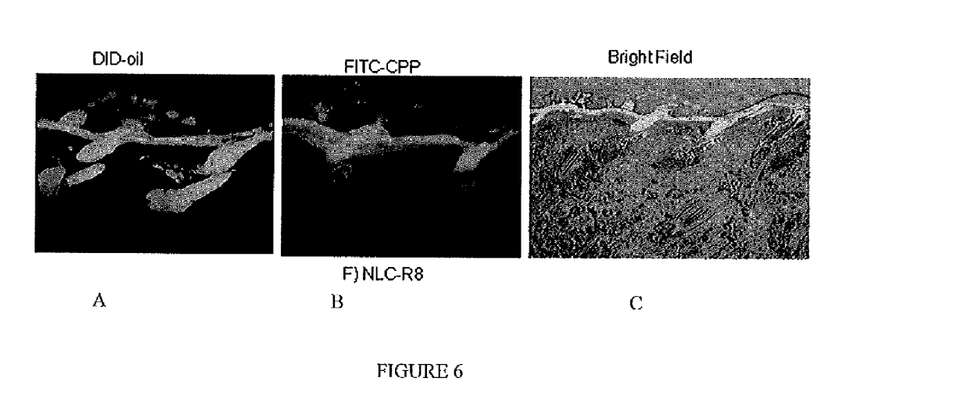
FIG. 6 illustrates rat skin permeation analysis of NLC-R8 microparticles encapsulating DID-oil dye over a 24 hour period. 6A illustrates the regular image, 6B illustrates the FITC labeled particles, and 6C illustrates the bright field image.
Figure 7:
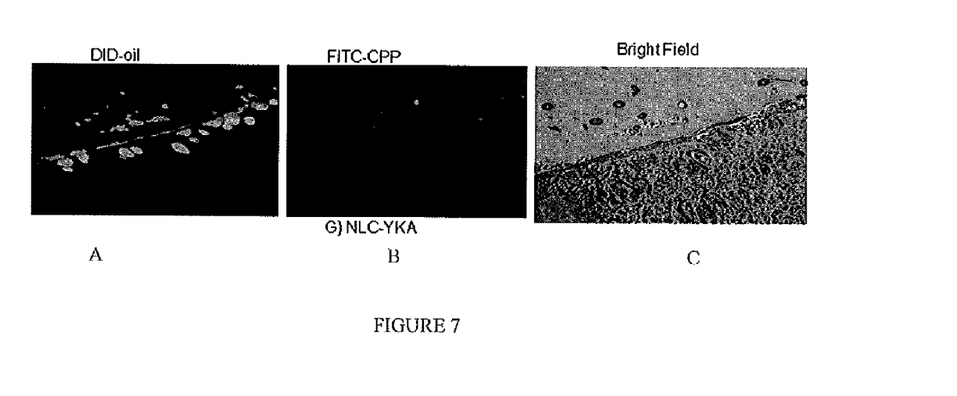
FIG. 7 illustrates rat skin permeation analysis of NLC-YKA microparticles encapsulating DID-oil dye over a 24 hour period. 7A illustrates the regular image, 7B illustrates the FITC labeled particles, and 7C illustrates the bright field image.
Figure 8:
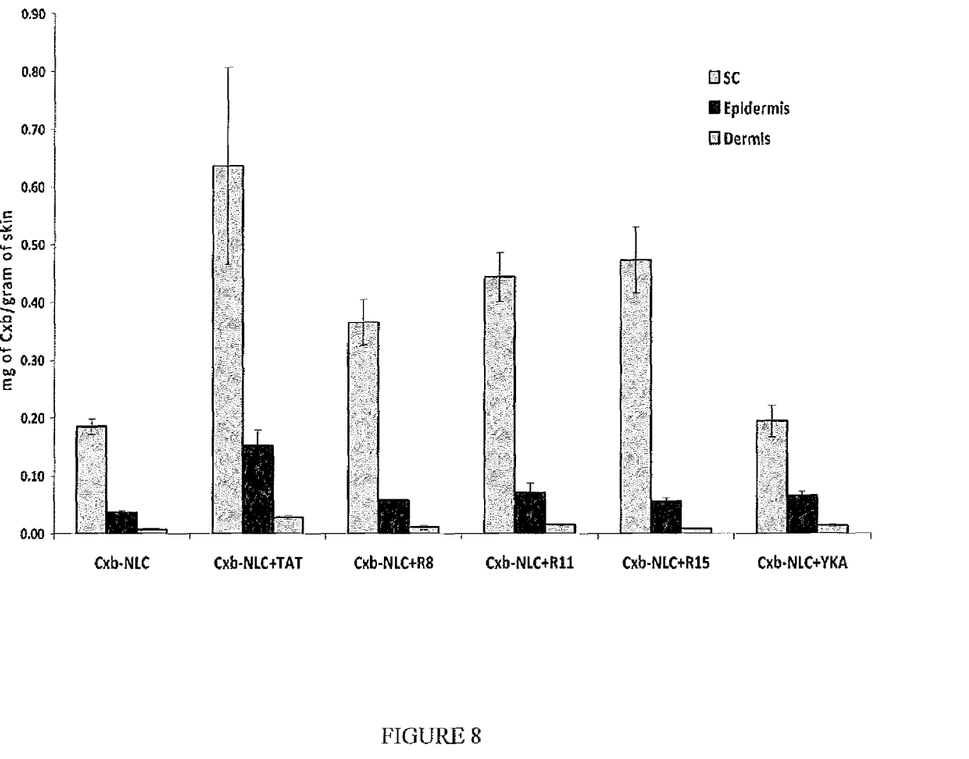
FIG. 8 is a graph of mg celecoxib per gram of rat skin after 24 hours. The CPPs used were TAT, R8, R11, R15, and YKA (See Table 1). The skin samples (SC, epidermis and dermis) were collected by cryotome sectioning. The data represent a replicate of four samples (n=4)±standard deviation.

Graph of Skin Permeation of the CX13-NLC:

Preliminary experiments were carried out to reproduce the observations made in the fluorescent visualization results and also to understand whether a CPP such as R11 would translocate the drug pay load in significant amounts into the skin. The first study was performed in dermatomed human cadaver skin and later optimized on the full thickness rat skin. FIG. 8 shows the effects of cell penetrating peptide on the CXB-NLC skin permeation at the end of a 24 hour period via full thickness rat skin. The skin samples (SC, epidermis and dermis) were collected after 24 hours by cryotome sectioning. In this experiment, the CPP peptides used were TAT, R8, R11 and R15 peptides. As a control, YKA (non-transduction peptide) was used. In the receptor fluid the CXB concentration was below detection limits. This observation was consistent with all CPPs tested. The data represent a replicate of four samples (n=4)±standard deviation.

Figure 9:
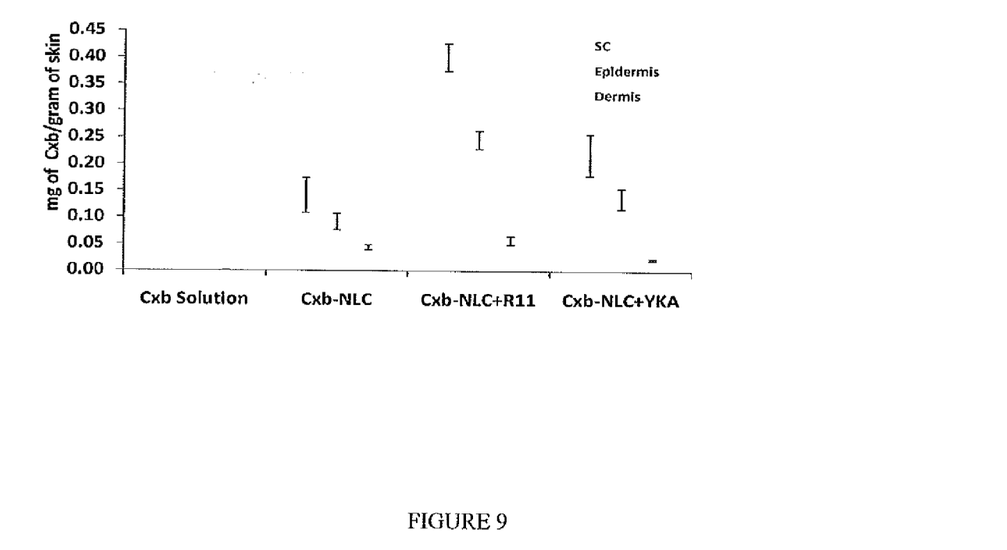
FIG. 9 illustrates human skin permeation of CXB-R11 after 24 hours. The skin samples (stratum corneum, epidermis and dermis) were collected by cryotome sectioning. As a control, YKA (non-transduction peptide) was used. The data represents replicate of four samples (n=4)±standard deviation.

FIG. 9 illustrates human skin permeation of CXB-NLCN formulations. The skin samples (stratum corneum, epidermis and dermis) collected after 24 hours were collected by cryotome sectioning. In this study, R11 peptide was used. As a control, YKA (non-transduction peptide) was used. In the receptor fluid the CXB concentration was below detection limits, this observation was consistent with all CPPs tested. The data represents replicate of four samples (n=4)±standard deviation.

FIGS. 8 and 9 confirm that surface modification of nanoparticles with cell penetrating peptide increased the skin permeation of encapsulated CXB. We believe that the observed 3-4 fold enhancement in stratum corneum and epidermis is mainly because of the number of CXB encapsulated nanoparticles entering into the skill is higher compared to CXB-NLC and nanoparticles coated with control peptide YKA formulations.

Example 4

Skin Permeation of Liposomes

The composition for the liposome formulation is shown in Table 5 below. The liposomes were prepared by solvent evaporation and dehydration method, wherein fluorescent dye FITC, DOPE, DOGS-NTA-Ni and POPC were dissolved in chloroform and ethanol (9:1) and a thin film was formed by evaporating the organic solvent in a round bottom flask at temperature of 60° C. under reduced pressure for 3-4 hours. Finally, the thin film was rehydrated with phosphate buffer saline (PBS), pH 7.4, and sonicated for 2-3 minutes in a bath sonicator. The particle size was measured with a Brookhaven Instrument (Holtsville, N.Y.) and found to be 147 nm respectively.

The liposome surface was modified by incubating with the TAT-6His peptide for 30 minutes at room temperature.

TABLE 5

| Fluorescent dye Encapsulated Liposome formulation | |
|---|---|
| Ingredients | Quantity (milligrams) |
| FITC | 1.0 |
| DOPE | 4.0 |
| POPC | 3.4 |
| DOGS-NTA-Ni | 0.5 |
| Phosphate buffer saline | 4 ml |

Figure 10:
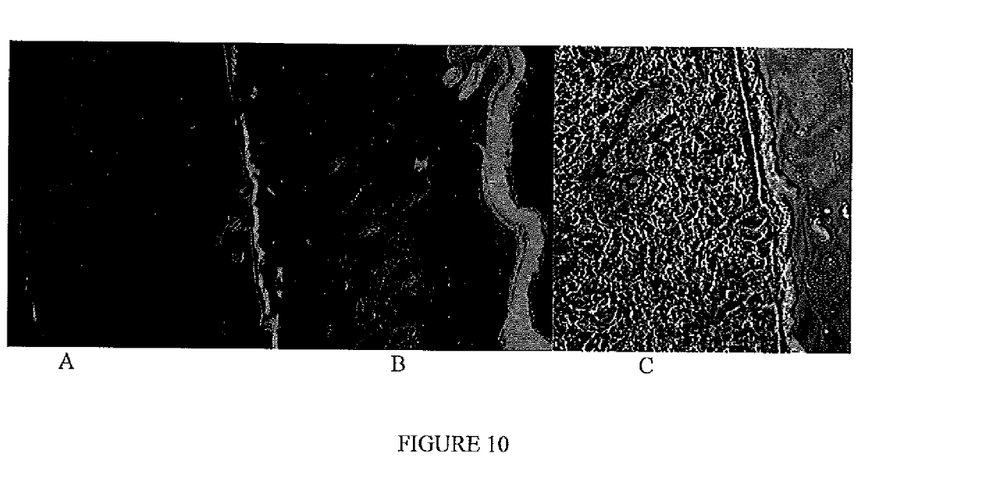
FIG. 10 illustrates rat skin permeation analysis of liposomes encapsulating FITC over a 6 hour period. 10A illustrates permeation of liposome without TAT, 10B shows binding of liposome+TAT, and 10C is the bright field image of 10A.

The images in FIG. 10 show skin permeation of liposomes whose surface was modified with TAT peptide. The rat skin permeation studies were carried out for 6 hours and the 30 μm thick skin sections were imaged under confocal microscope. The images confirm that surface modification of liposomes with TAT peptide enhanced the skin permeation of liposomes.

Modifications and variation of the present invention will be apparent to those skilled in the art from the forgoing detailed description. All modifications and variations are intended to be encompassed by the following claims. All publications, patents and patent applications cited herein are incorporated by reference in their entirety.

The invention claimed is:

1. A formulation for topical application to a selected target skin tissue in the skin of a subject,
   wherein said formulation comprises nanostructured lipid carrier nanoparticles encapsulating an active substance,
   wherein the surface of the nanoparticles is modified with a cell penetrating peptide, and
   wherein the nanoparticles comprise a blend of solid lipids and liquid lipids,
   wherein the blend is solid at body temperature, and
   wherein the formulation releases the active substance in a controlled manner upon application to the skin so that it penetrates the skin and is delivered to the epidermis to a depth of from about 80 to about 120 microns.

2. The formulation of claim 1, wherein the solid lipids are comprised of oil-based or lipidic medium carriers and the liquid lipids are comprised of an organic phase.

3. The formulation of claim 1, wherein the active substance is an anti-inflammatory agent.

4. The formulation of claim 1, wherein the active substance is suitable for the treatment of a disease or condition which is localized, or at least partially localized to the skin.

5. The formulation of claim 1, wherein the disease or condition is selected from the group consisting of psoriasis, irritant contact dermatitis, atopic dermatitis, contact dermatitis, inflammation, eczema, infections including bacterial and fungal infections, acne, rheumatoid arthritis and skin cancer.

6. The formulation of claim 1, wherein the solid lipids are selected from the group consisting of mono-, di- and triglycerides or mixtures thereof and nickel chelating lipids, and the liquid lipids are surfactants.

7. The formulation of claim 1, wherein the cell penetrating peptide is selected from the group consisting of a transactivating transcriptional activator protein (TAT), YARA, penetratin, and polyarginine ($R_n$) where Rn is $Arg_8$, $Arg_{11}$ or $Arg_{15}$.

8. The formulation of claim 7, wherein the TAT is Gly-Tyr-Arg-Lys -Lys-Arg-Arg-Gln-Arg-Arg-Arg-His-His-His-His-His-His.

9. The formulation of claim 1, wherein the cell penetrating peptides are attached to the nanoparticles with DOGS-NTA-Ni chelating lipid.

10. The formulation of claim 1, wherein the cell penetrating peptide is a polyarginine ($R_n$) where n is 8, 11, or 15.

* * * * *

UNITED STATES PATENT AND TRADEMARK OFFICE
CERTIFICATE OF CORRECTION

PATENT NO. : 8,715,736 B2  
APPLICATION NO. : 12/433344  
DATED : May 6, 2014  
INVENTOR(S) : Mandip Singh Sachdeva and Ram Patlolla It is certified that error appears in the above-identified patent and that said Letters Patent is hereby corrected as shown below:

Column 1, Line 7, should read as follows

This invention was made with government support under grant number 36458 awarded by National Institutes of Health/NIAMS. The government has certain rights in the invention.

Signed and Sealed this
Third Day of November, 2015

Michelle K. Lee
*Director of the United States Patent and Trademark Office*

```
SEQUENCE LISTING

<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<223> OTHER INFORMATION: synthetically generated peptide

<400> SEQUENCE: 1

Tyr Gly Arg Lys Lys Arg Arg Gln Arg Arg Arg His His His His His
1               5                   10                  15

His

<210> SEQ ID NO 2
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 2

Tyr Ala Arg Ala Ala Ala Arg Gln Ala Arg Ala
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetically generated peptide

<400> SEQUENCE: 3

Arg Arg Arg Arg Arg Arg Arg Arg His His His His His His
1               5                   10

<210> SEQ ID NO 4
<211> LENGTH: 17
<212> TYPE: PRT
<213> ORGANISM: Artificial Sequence
```

```
-continued

<220> FEATURE:
<223> OTHER INFORMATION: synthetically generated peptide

<400> SEQUENCE: 4

Arg Arg Arg Arg Arg Arg Arg Arg Arg Arg Arg His His His His His
1               5                   10                  15

His

<210> SEQ ID NO 5
<211> LENGTH: 21
<212> TYPE: PRT
<213> ORGANISM: Artificial Sequence
<220> FEATURE:
<223> OTHER INFORMATION: synthetically generated peptide

<400> SEQUENCE: 5

Arg Arg Arg Arg Arg Arg Arg Arg Arg Arg Arg Arg Arg Arg Arg His
1               5                   10                  15

His His His His His
            20

<210> SEQ ID NO 6
<211> LENGTH: 18
<212> TYPE: PRT
<213> ORGANISM: Artificial Sequence
<220> FEATURE:
<223> OTHER INFORMATION: syntheticall generated peptide

<400> SEQUENCE: 6

Tyr Lys Ala Leu Arg Ile Ser Arg Lys Leu Ala Lys His His His His
1               5                   10                  15

His His
```